United States Patent
Kottayil et al.

(10) Patent No.: US 12,285,420 B2
(45) Date of Patent: *Apr. 29, 2025

(54) STABLE NIMODIPINE PARENTERAL FORMULATION

(71) Applicant: ACASTI PHARMA U.S., INC., Wilmington, DE (US)

(72) Inventors: S. George Kottayil, West Windsor, NJ (US); Amresh Kumar, Plainsboro, NJ (US); Prasanna Sunthankar, West Windsor, NJ (US); Vimal Kavuru, Holmdel, NJ (US); Kamalkishore Pati, Old Bridge, NJ (US)

(73) Assignee: ACASTI PHARMA U.S., INC., Wilmington, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 18/758,839

(22) Filed: Jun. 28, 2024

(65) Prior Publication Data

US 2024/0350473 A1  Oct. 24, 2024

Related U.S. Application Data

(63) Continuation of application No. 17/523,334, filed on Nov. 10, 2021, now Pat. No. 12,059,415, which is a continuation of application No. 16/281,676, filed on Feb. 21, 2019, now abandoned.

(60) Provisional application No. 62/633,863, filed on Feb. 22, 2018.

(51) Int. Cl.
```
A61K 9/00      (2006.01)
A61K 31/451    (2006.01)
A61K 47/10     (2017.01)
A61K 47/26     (2006.01)
A61P 9/04      (2006.01)
A61P 9/06      (2006.01)
A61P 9/10      (2006.01)
A61P 9/12      (2006.01)
A61P 9/14      (2006.01)
```

(52) U.S. Cl.
CPC .......... *A61K 31/451* (2013.01); *A61K 9/0019* (2013.01); *A61K 47/10* (2013.01); *A61K 47/26* (2013.01); *A61P 9/04* (2018.01); *A61P 9/06* (2018.01); *A61P 9/10* (2018.01); *A61P 9/12* (2018.01); *A61P 9/14* (2018.01)

(58) Field of Classification Search
CPC .... A61K 31/451; A61K 9/0019; A61K 47/10; A61K 47/26; A61P 9/10; A61P 9/06; A61P 9/12; A61P 9/04; A61P 9/14
See application file for complete search history.

(56) References Cited

U.S. PATENT DOCUMENTS

| | | | |
|---|---|---|---|
| 4,879,308 A | 11/1989 | Alam et al. | |
| 10,092,553 B2 | 10/2018 | Kottayil et al. | |
| 10,092,557 B2 | 10/2018 | Kottayil et al. | |
| 2004/0180005 A1* | 9/2004 | Jurgens | A61K 9/1075 424/46 |
| 2004/0247624 A1 | 12/2004 | Unger et al. | |
| 2007/0117851 A1* | 5/2007 | Remenar | A61P 9/00 514/355 |
| 2009/0253722 A1 | 10/2009 | Gillessen et al. | |
| 2012/0177699 A1* | 7/2012 | Tong | A61P 29/00 514/356 |
| 2013/0156853 A1 | 6/2013 | Zhang et al. | |
| 2017/0296522 A1 | 10/2017 | Kottayil et al. | |
| 2017/0296527 A1 | 10/2017 | Kottayil et al. | |

FOREIGN PATENT DOCUMENTS

| | | |
|---|---|---|
| CN | 1 771 950 A | 5/2006 |
| CN | 101045054 A | 10/2007 |
| CN | 101129366 | 2/2008 |
| CN | 102525917 | 7/2012 |

OTHER PUBLICATIONS

Wikipedia, Polysorbate, Jan. 29, 2016, p. 1/2; <https://en.wikipedia.org/wiki/Polysorbate>.
Kalepu et al. "Insoluble drug delivery strategies: review of recent advances and business prospects" Acta Pharmaceutica Sinica B, vol. 5, No. 5, pp. 442-453; p. 445 (May 26, 2015).
Stagliano "Do mirrors reflect ultraviolet light?" (Dec. 24, 2014), <https://www.quora.com/Do-mirrors-reflect-ultraviolet-light>.
International Search Report from International PCT Application No. PCT/US2017/027164 dated Jul. 21, 2017.
Pizarro et al. "Photophysical and photochemical behavior of nimodipine and felodipine" Journal of Photochemistry and Photobiology A: Chemistry, Jun. 10, 2007, vol. 189, pp. 23-29; p. 23.
U.S. Appl. No. 16/046,487, filed Jul. 26, 2018, Kottayil et al.
International Search Report from International PCT Application No. PCT/US2018/40038 dated Aug. 31, 2018.
"Nimotop 0.02% Solution for Infusion" Summary of Product Characteristics (SmPC)—(eMC) https://www.medicines.org.uk/emc/product/1366/smpc pp. 1-9; date of first authorization: Jan. 21, 1988/ Nov. 23, 2003/ Date of revision of the text Aug. 31, 2017.

(Continued)

Primary Examiner — Jianfeng Song
(74) Attorney, Agent, or Firm — Davidson Kappel LLC

(57) ABSTRACT

A nimodipine injection concentrate and diluted formulation comprises nimodipine (base or salt), an effective amount of a hydrophilic surfactant, and a pharmaceutically acceptable carrier for injection which is an aqueous solution substantially free of organic solvent, such that the nimodipine is substantially contained in a concentrated injection solution, suspension, emulsion or complex as a micelle or a colloidal particle or an inclusion complex and the formulation is stable and clear. In certain embodiments, the hydrophilic surfactant is polysorbate 80.

11 Claims, No Drawings

(56) References Cited

OTHER PUBLICATIONS

"Nimotop (nimodipine) Capsules for Oral Use" FDA approved Labeling text, Bayer Pharmaceuticals Corporation, pp. 1-8 (Dec. 2005).
"Product Information Nimotop nimodipine" Bayer Australia Ltd; (Jun. 9, 1993); date of most recent amendment (Apr. 18, 2017).
International Search Report from the International PCT Application No. PCT/US19/18945 dated Apr. 24, 2019.
Teagarden, DL, et al. "Freeze Drying/Lyophilization of Pharmaceutical and Biological Products" Informa healthcare. Drugs and The Pharmaceutical Sciences, Third Edition, 2010, vol. 206; 276, Miscellaneous Pharmaceutical Uses-Liposomes section.
International Written Opinion from the International PCT Application No. PCT/US19/18945 dated Apr. 24, 2019.

* cited by examiner

STABLE NIMODIPINE PARENTERAL FORMULATION

This application is a continuation of U.S. patent application Ser. No. 17/523,334, filed Nov. 10, 2021, which is a continuation of U.S. patent application Ser. No. 16/281,676, filed Feb. 21, 2019, which claims the benefit of U.S. Provisional Application No. 62/633,863, filed Feb. 22, 2018, the disclosures of which is hereby incorporated by reference in their entirety.

FIELD OF THE INVENTION

The present invention provides a stable nimodipine concentrate and parenteral solution suitable for continuous intravenous (IV) administration. The parenteral solution composition consists of an aqueous solution of nimodipine (concentrations ranging from about 0.5 to about 50 mg/ml), a hydrophilic surfactant and an aqueous solvent, wherein the formulation is essentially free of organic solvents.

BACKGROUND OF THE INVENTION

Nimodipine, a lipid soluble substituted 1, 4-dihydropyridine with vasodilatatory properties, is indicated for prophylaxis and treatment of ischemic neurologic deficits caused by cerebral vasospasms after subarachnoid hemorrhage (SAH). Currently, nimodipine treatment of ischemic brain injury is the first-line treatment. In man, nimodipine is rapidly absorbed after oral administration, and peak concentrations are generally attained within one hour. The terminal elimination half-life is approximately 8 to 9 hours but earlier elimination rates are much more rapid, equivalent to a half-life of 1-2 hours; a consequence is the need for frequent (every 4 hours) dosing. Nimodipine is eliminated almost exclusively in the form of metabolites and less than 1% is recovered in the urine as unchanged drug. Numerous metabolites, all of which are either inactive or considerably less active than the parent compound, have been identified. Because of a high first-pass metabolism, the bioavailability of nimodipine averages 13% after oral administration. The bioavailability is significantly increased in patients with hepatic cirrhosis, with Cmax approximately double that in normal, which necessitates lowering the dose in this group of patients.

Currently approved products in the US market are oral solid and liquid dosage forms of nimodipine. Nimodipine is marketed in the US as an oral dosage form, NIMOTOP® liquid-filled capsules (Bayer Pharmaceuticals Corp.) and equivalent generics. NIMOTOP® capsules and generic versions of the same each contain 30 mg of nimodipine and are commonly administered in a two-capsule 60 mg dose, and dosed every 4 hours. In the event that a patient is unconscious or unable to swallow, the nimodipine capsule contents are extracted by syringe and administered via an intraoral or an intranasal (e.g., naso-gastric) tube. The medical practitioner administering the dose may either unknowingly or due to improper handling, extract less than the full amount of the liquid dose from the capsule, thus introducing substantial risk of incomplete dosing and placing undue burden on medical professionals. The incomplete dosing is exacerbated by the relatively small dosage volumes involved and high drug concentration of drug in the commercially available capsules. Hence, a practitioner's failure to dose the full amount of the high-concentration, small volume liquid from the commercial capsules could lead to a significant under dose of nimodipine. Also, the FDA has noted in warnings related to oral nimodipine administration via nasogastric tubes that because a standard needle does not fit on an oral syringe, the formulation within a capsule is extracted using an intravenous syringe. The use of intravenous syringes to extract nimodipine formulation from the capsule increases the chance of medication being inadvertently administered intravenously instead of by mouth or nasogastric tube.

To quickly and effectively treat or control disease progression following SAH, intravenous administration of nimodipine is usually preferred. Intravenous (IV) Nimodipine is approved in Europe and marketed in Europe by Bayer under the trade name Nimotop®. The current commercially marketed injectable nimodipine (Bayer's Nimotop®) available in Europe and other regulated markets contains large amounts of organic solvent—about 23.7% ethanol (alcohol) and 17% polyethylene glycol 400, i.e. up to 50 g per daily dose (250 ml), equivalent to 1200 ml beer (5 vol %) or 500 ml wine (12 vol %) per dose. The large amount of ethanol in Nimotop is harmful for those suffering from alcoholism or impaired alcohol metabolism and in pregnant or breast feeding women. Also, high concentrations of ethanol may cause pain and irritation at the injection site. IV Nimotop is most often infused continuously up to three weeks. Due to the high alcohol content in Bayer's IV Nimotop solution, it is diluted by co-infusing saline and dextrose by way of a three-way stopcock. This may be harmful for those suffering from alcoholism or impaired alcohol metabolism and should be taken into account in pregnant or breast-feeding women, children and high-risk groups such as patients with liver disease or epilepsy. The amount of alcohol in this medicine may alter the effects of other medicines. Nimodipine has poor water solubility and is therefore difficult to formulate as an aqueous injectable. That is the reason that Nimotop IV infusion solution utilizes up to 23.7% of alcohol as a co-solvent to solubilize nimodipine.

U.S. Pat. No. 5,114,956 describes parenteral formulations containing nimodipine, that contain 0.01-0.4% by weight of nimodipine, relative to 100 parts by weight of a solvent consisting of 30-70% by weight, preferably 45-70% by weight, of water, 15-40% by weight, preferably 15-30% by weight, of propylene glycol and/or polyethylene glycol, preferably with a mean molecular weight of 200, 400 and 600, 15-30% by weight, preferably 15-25% by weight, of ethanol, and, where appropriate, customary auxiliaries and/or additives.

Through its Adverse Event Reporting System (AERS) and other sources, including published literature, the FDA has identified 31 cases of nimodipine errors between 1989 and 2009, with 25 involving the administration of the contents of the oral capsule intravenously according to the FDA. Four patients who received nimodipine intravenously died, while another 5 suffered severe reactions and one patient suffered permanent harm, according to the agency.

Previously, our U.S. Pat. Nos. 10,092,557 and 10,092,553 disclosed a nimodipine injection concentrate and diluted formulation comprises nimodipine (base or salt), an effective amount of a hydrophilic surfactant, and a pharmaceutically acceptable carrier for injection which is an aqueous solution, an organic solvent, an oil, or a cyclodextrin, such that the nimodipine is substantially contained in a concentrated injection solution, suspension, emulsion or complex as a micelle or a colloidal particle or an inclusion complex and the formulation is stable and clear. In certain embodiments, the hydrophilic surfactant is polysorbate 80. The diluted formulation which is a stable directly infusible nimodipine formulation suitable for parenteral administration in humans, comprises nimodipine in a concentration from about 0.01 mg/ml to about 1.0 mg/ml, surfactant (e.g., polysorbate 80), and a pharmaceutically acceptable organic solvent comprising less than 2% w/v of the formulation.

There exists an unmet medical need for an easy to administer nimodipine dosage form for patients who find it difficult or are unable to swallow and patients who are unconscious. There exists a further unmet medical need for a nimodipine formulation which includes little or no organic solvent but yet is stable (e.g., the formulation is a clear colorless liquid and does not include a crystalline nimodipine precipitate). An additional imperative is the need to eliminate serious life-threatening medication errors as a result of improper administration of drug.

As per the European Commission guideline on 'Excipients in the labelling and package leaflet of medicinal products for human use' (SANTE-2017-11668) mentioned in below table, for parentral route of administration the recommended dose of less than 100 mg per dose and or 1-6 mg/kg/day is preferred. There exists a further unmet medical need for a nimodipine formulation which includes little or no organic solvent but yet is stable (e.g., the formulation is a clear colorless liquid and does not include a crystalline nimodipine precipitate).

Another objective of the present invention is to provide compositions that make it possible either to reduce the ethanol concentrations greatly, or to eliminate ethanol completely from the intravenous nimodipine infusion formulation.

Another objective of the present invention is to provide injectable nimodipine formulations which include little or no alcohol, but yet provide a stable formulation which does not include a crystalline nimodipine precipitate and is clear and colorless.

In accordance with the above objects and others, the invention is directed to a nimodipine concentrate formulation, consisting of nimodipine base or a pharmaceutically acceptable salt of nimodipine in an aqueous carrier from about 0.5 mg/ml to about 50 mg/ml, preferably from about 10 mg/ml to about 50 mg/ml, in an aqueous carrier, and an effective amount of a hydrophilic surfactant, the formulation being lyophilized such that it is substantially free from organic solvent or contains from about 0 to about 0.5% organic solvent, the nimodipine in the concentrate formulation contained in micelles, the concentrate formulation further comprising an optional preservative, and an optional buffering agent, the concentrate formulation being clear, colorless, stable, and without or substantially without crys-

| Name | Route of Administration | Threshold | Information for the Package Leaflet | Comments |
|---|---|---|---|---|
| Ethanol | Oral, parenteral | Less than 100 mg per dose | This medicinal product contains small amounts of ethanol (alcohol), less than 100 mg per <dose>. | This statement is to provide reassurance to parents and children concerning the low levels of alcohol in the product. |
| Ethanol | Oral, parenteral | 100 mg per dose | This medicinal product contains . . . vol % ethanol (alcohol), i.e. up to . . . mg per <dose>, equivalent to . . . ml beer, . . . ml wine per <dose>. Harmful for those suffering from alcoholism. To be taken into account in pregnant or breast-feeding women, children and high-risk groups such as patients with liver disease, or epilepsy. | The package leaflet should give the equivalent volume of beer and wine, nominally calculated assuming 5% vol and 12% vol ethanol respectively. Separate warning statements may be needed in different parts of the PL. |
| Ethanol | Oral, parenteral | 3 g per dose | This medicinal product contains . . . vol % ethanol (alcohol), i.e. up to . . . mg per <dose>, equivalent to . . . ml beer, . . . ml wine per <dose>. Harmful for those suffering from alcoholism. To be taken into account in pregnant or breast-feeding women, children and high-risk groups such as patients with liver disease or epilepsy. The amount of alcohol in this medicinal product may alter the effects of other medicines. The amount of alcohol in this medicinal product may impair your ability to drive or use machines. | |

Reference: Annex to the European Commission guideline on 'Excipients in the labelling and package leaflet of medicinal products for human use' (SANTE-2017-11668). EMA/CHMP/302620/2017/EN

OBJECTS AND SUMMARY OF THE INVENTION

The present invention aims to resolve solubility deficiencies of previously approved nimodipine dosage forms by the development of a robust, stable, and easy to administer nimodipine infusion injection.

Another objective of the present invention is to provide the composition and preparation of the nimodipine infusion solution and its administration.

talline nimodipine precipitate. In other preferred embodiments, the invention is directed in part to a nimodipine concentrate formulation, comprising nimodipine base or a pharmaceutically acceptable salt of nimodipine in an aqueous carrier comprising from about 10 mg/ml to about 50 mg/ml nimodipine for a total dose of about 10 mg (based on nimodipine base), an effective amount of a hydrophilic surfactant such that nimodipine in the concentrate formulation is contained in micelles, and from about 0 to about 300 mg organic solvent, the concentrate formulation being clear, colorless, stable, and does not contain a crystal nimodipine precipitate. Preferably, the concentrate formulation is suitable for injection when diluted with further aqueous carrier. In preferred embodiments, the hydrophilic surfactant comprises from about 1% to about 99.5% of the concentrate formulation. In certain embodiments, the hydrophilic surfactant is polysorbate 80. In certain embodiments, the pharmaceutically acceptable carrier is water for injection. In certain embodiments, a unit dose of the concentrate is diluted to a total volume of 5 ml with water for injection and enclosed within a pharmaceutically acceptable container, e.g., an ampule or vial. In certain embodiments, the nimodipine injection concentrate further comprises an effective amount of a preservative. In certain preferred embodiments, the median particle size of micelles or nano-emulsions ranges from about 0.5 nanometer to about 350 nanometers, or from about 0.5 nm to about 200 nm, or from about 5 nm to about 50 nm. In certain preferred embodiments, the organic solvent included in the initial preparation of the concentrate formulation is substantially or completely removed by evaporation under vacuum or another suitable process known to those skilled in the art. Thus, in certain preferred embodiments, the nimodipine concentrate formulation contains less than 1% w/v organic solvent, and in most preferred embodiments the nimodipine concentrate formulation is substantially free or totally free of organic solvents/alcohol, e.g., such that the nimodipine concentrate formulation contains from about 0 to about 300 mg alcohol per dose per 10 mg dose of nimodipine, and preferably about 100 mg or less alcohol per 10 mg dose of nimodipine and/or 1-6 mg/kg/day. In certain preferred embodiments, the nimodipine is substantially contained within micelles as a nano-emulsion.

The invention is further directed in part to a nimodipine infusion formulation, comprising a nimodipine base or a pharmaceutically acceptable salt of nimodipine and an effective amount of a hydrophilic surfactant consisting of polysorbate 80 lyophilized or vacuumed dried to a nimodipine concentrate to remove alcohol or other organic solvent, the lyophilized nimodipine concentrate diluted with a pharmaceutically acceptable aqueous carrier for injection such that the nimodipine infusion formulation can be administered at an infusion rate of nimodipine from about 0.5 mg/hr to about 2.5 mg/hr and such that the infusion does not provide alcohol in an amount of more than 6 mg/kg/day when infused into a human patient, the formulation further comprising an optional preservative and an optional buffering agent, the nimodipine infusion formulation being clear, colorless, stable, and without crystalline nimodipine precipitate. The nimodipine in the nimodipine concentrate formulation is preferably contained in micelles at a concentration from about 10 mg/ml to about 50 mg/ml, and wherein the nimodipine in the nimodipine infusion formulation is contained in micelles at a concentration from about 0.0.001 mg/ml to about 0.5 mg/ml. The polysorbate 80 preferably comprises from about 40% to about 99% of the injection concentrate and the polysorbate 80 comprises less than 1% of the nimodipine infusion formulation. The organic solvent is preferably dehydrated alcohol and the aqueous carrier is preferably selected from the group consisting sodium chloride injection, Ringers injection, isotonic dextrose injection, sterile water for injection, dextrose, Lactated Ringers injection, and total parenteral nutrition (TPN). The invention is further directed to a method of treatment, comprising intravenously administering the nimodipine infusion formulation to a human patient at a nimodipine infusion rate of from about 2 to 10 mg every five hours, or, e.g., from about 8 mg/day to about 50 mg/day.

The present invention is further directed in part to a nimodipine solution suitable for injection, which can be prepared from the above-described nimodipine concentrate which is diluted in a pharmaceutically acceptable medium (e.g., saline to provide a physiologically and pharmaceutically acceptable formulation) to a solution for administration by infusion. The nimodipine solution comprises from about 0.01 mg/ml to about 1.0 mg/ml nimodipine or a pharmaceutically acceptable salt thereof in an aqueous carrier suitable for injection, and an effective amount of a hydrophilic surfactant such that nimodipine in the concentrate formulation is contained in micelles, the nimodipine formulation having a volume from about 50 ml to about 1000 ml and being clear, colorless and does not contain a crystal nimodipine precipitate. In preferred embodiments, the nimodipine solution contains from about 0.01% to about 5% w/v of the hydrophilic surfactant. In preferred embodiments, the nimodipine solution allows for parenteral administration of a single 250 ml infusion bag or bottle to a human patient, the diluted formulation containing less than about 2%, more preferably less than about 1% w/v, or is substantially free of organic solvent (e.g., alcohol). In certain embodiments, the nimodipine solution further comprises an effective amount of a pharmaceutically acceptable preservative. In certain preferred embodiments, substantially all or all of the nimodipine contained in the formulation is contained in micelles or nano-emulsions. The concentrate and dilution prepared from the concentrate preferably includes a low alcohol content, e.g., preferably less than 300 mg per dose (e.g., per 10 mg dose of nimodipine), and in certain preferred embodiments less than 200 mg alcohol per dose (per 10 mg dose of nimodipine), or less than 100 mg alcohol per dose, or less than 50 mg alcohol per dose, or less than 25 mg alcohol per dose (per 10 mg dose of nimodipine), or less than 10 mg alcohol per dose (per 10 mg dose of nimodipine), or less than 5 mg alcohol per dose (per 10 mg dose of nimodipine). Expressed in another way, in preferred embodiments, the concentrate and dilution prepared from the concentrate preferably includes a low alcohol content, e.g., preferably from about 0 to about 300 mg per dose (e.g., per 10 mg dose of nimodipine), or from about 0 to about 200 mg alcohol per dose (per 10 mg dose of nimodipine), or from about 0 to about 100 mg per dose (e.g., per 10 mg dose of nimodipine), or from about 0 to about 50 mg alcohol per dose (per 10 mg dose of nimodipine), or from about 0 to about 25 mg per dose (e.g., per 10 mg dose of nimodipine), or from about 0 to about 10 mg alcohol per dose (per 10 mg dose of nimodipine), or from about 0 to about 5 mg alcohol per dose (per 10 mg dose of nimodipine). Preferably, the volume of the nimodipine solution can be, e.g., from about 50 ml to 1000 ml, with a concentration of from about 0.01 mg/ml to about 1.0 mg/ml nimodipine. Preferably, when diluted the nimodipine solution will have less than about 300 mg alcohol contained in that volume (of from about 50 ml to 1000 ml). In certain preferred embodiments of the nimodipine solution (after dilution of the afore-mentioned concentrate above), the median particle size of micelles or nano-emulsions range from about 0.5 nanometer to about 350 nanometers, or from about 0.5 nm to about 200 nm, or from about 5 nm to about 50 nm. Preferably, the nimodipine concentrate after dilution composition is clear and does not contain a crystal nimodipine precipitate. In certain preferred embodiments, the nimodipine is substantially contained within micelles as a nano-emulsion.

In other embodiments, the invention is directed in part to a method of preparing a nimodipine injection concentrate the solution having a low ethanol content. This is accomplished by first dissolving nimodipine or a pharmaceutically acceptable salt thereof in an organic solvent (e.g., ethanol) and surfactant to form a nimodipine concentrate, the surfactant being in an amount effective to enable the formation of micelles in the surfactant. Thereafter, the concentrate is diluted in a pharmaceutically acceptable aqueous medium. The organic solvent (e.g., ethanol) contained in this concentrate solution is then substantially removed by evaporation under vacuum or by any other suitable means. After evaporation of the organic solvent (e.g., ethanol), the concentrate formulation preferably contains from about 0.5 mg/ml to about 50 mg/ml of nimodipine in a mixture containing from about 1% to about 99.5% of hydrophilic surfactant. The resultant nimodipine concentrate is stable, clear, colorless, free from crystalline nimodipine precipitate, and substantially, if not totally alcohol free. In certain preferred embodiments of the nimodipine injection concentrate, the median particle size of micelles or nano-emulsions ranges from about 0.5 nanometer to about 350 nanometers, or from about 0.5 nm to about 200 nm, or from about 5 nm to about 50 nm.

The invention is further directed to a method of preparing a nimodipine concentrate formulation, comprising mixing nimodipine base or a pharmaceutically acceptable nimodipine salt with an organic solvent in an amount sufficient to dissolve the nimodipine; adding a hydrophilic surfactant to the mixture of nimodipine and organic solvent; diluting the mixture with an aqueous carrier; and thereafter substantially removing organic solvent via lyophilization to obtain a nimodipine concentrate that contains from about 0.5 mg/ml to about 50 mg/ml, and preferably from about 10 mg/ml to about 50 mg/ml nimodipine in micelles, the concentrate formulation being clear, colorless, stable, and without a crystal nimodipine precipitate. The method may further comprise storing the nimodipine concentration formulation with degassing and headspace replacement with an inert gas. In certain preferred embodiments, the lyophilization is continued until the nimodipine concentrate formulation comprises from about 0.5 mg/ml to about 50 mg/ml nimodipine and preferably from about 10 mg/ml to about 50 mg/ml, for a total dose of about 10 mg nimodipine, and from about 0 to about 300 mg organic solvent, or from about 0 to about 200 mg organic solvent, or from about 0 to about 100 mg organic solvent. In certain preferred embodiments, the aqueous carrier is deoxygenated water, the organic solvent is dehydrated alcohol, and the hydrophilic surfactant comprises polysorbate 80. In certain embodiments, the invention further comprises diluting the nimodipine concentrate formulation to a volume from about 50 ml to about 1000 ml with a pharmaceutical acceptable carrier for injection such that the nimodipine is present in a concentration from about 0.01 mg/ml to about 1.0 mg/ml, preferably from about 0.001 mg/ml to about 0.5 mg/ml, the diluted formulation remaining clear micellar solution and displaying no crystal precipitation of nimodipinc.

In certain preferred embodiments, the nimodipine is substantially contained within micelles as a nano-emulsion. In certain preferred embodiments, the formulation is stable when exposed to conditions of 40° C.±2° C./75% RH±5% RH for at least 6 months; and/or which is stable when exposed to conditions of 25° C.±2° C./60% RH±5% RH for at least 12 months.

In certain preferred embodiments, the nimodipine concentrate has a volume from about 0.1 ml to about 10 ml, preferably about 1 ml, and is contained in an ampoule or vial.

In certain embodiments, the nimodipine injection concentrate is diluted with water for injection, saline, dextrose or other commonly available infusion solutions up to a concentration, e.g., from about 0.01 mg/ml to about 1.0 mg/ml nimodipine and remains a clear solution and displays no crystal precipitation of nimodipine. The nimodipine injection concentrate can preferably be diluted with a suitable injection medium that allows for administration of, e.g., a single 100 or preferably 250 ml infusion bag or bottle that contains, e.g., less than 1% w/v alcohol in a predominantly aqueous medium, the diluted injection medium remaining a clear solution that displays no precipitation of nimodipine.

In certain preferred embodiments, the emulsifier is selected from the group consisting of a phospholipid and a polyethylene glycol.

In certain preferred embodiments, the nimodipine formulation is contained within a single infusion bag or bottle for continuous intravenous infusion.

The administration of the nimodipine formulation via injection or infusion allows first pass metabolism of the nimodipine by the liver to be minimized, and the nimodipine formulations administered via injection have significantly improved bioavailability as compared to oral nimodipine formulations. By virtue of the nimodipine injectable formulations of the invention, consistent levels of nimodipine can be maintained in the plasma and CSF of the (e.g., human) patient.

In alternative embodiments to the above, the nimodipine formulation is diluted with a suitable pharmaceutical carrier for oral or nasal ingestion (e.g., a suitable aqueous solution).

In certain preferred embodiments of the above-described nimodipine concentrate and formulation, the aqueous carrier is selected from the group consisting of Sodium Chloride Injection, Ringers Injection, Isotonic Dextrose Injection, Sterile Water Injection, Dextrose, and Lactated Ringers Injection.

In certain preferred embodiments, the nimodipine formulation further comprises one or more preservatives. Examples of suitable preservatives include, e.g., phenols or cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quarternary compounds, mercurials, and mixtures of any of the foregoing.

In certain preferred embodiments of the nimodipine concentrate formulation, the pharmaceutically acceptable carrier comprises from about 0.1% to about 99.5% of the formulation.

In certain preferred embodiments, the nimodipine formulation has a pH from about 3 to about 9, and in certain preferred embodiments, preferably from about 4.5 to about 7.5 or 8.

The invention is further directed to a method of treating human patients having a condition selected from an aneurysm, subarachnoid hemorrhage, vasospastic angina, Prinzmetal angina, stable angina, acute myocardial infarction, myocardial arrest, arrhythmia, systemic hypertension, pulmonary hypertension, congestive heart failure, coronary artery surgery and hypertrophic cardiomyopathy, comprising continuously infusing an intravenous nimodipine solution in accordance with the present invention over a period of about three weeks. The nimodipine infusion rate may be, e.g., from about 0.05 mg nimodipine per hour to about 5 mg nimodipine per hour. In certain embodiments, the intravenous nimodipine dose is from about 2 to 10 mg administered every five hours. In certain embodiments, the nimodipine formulation is administered via intravenous bolus, intravenous infusion, intra-arterial, intraoral, or intranasal using a naso-gastric tube. In certain embodiments, the method further comprises further diluting to a $2.5 \times 10^{-5}$ mole solution of nimodipine to rinse the exposed arteries after clipping the aneurysm and before an intravenous infusion of nimodipine administered to improve patient outcome. The diluted formulation may be contained within an infusion set and bag. In further embodiments, the infusion bag is covered with ultraviolet light (UV) protective bags to further protect the nimodipine from photo-degradation. In other preferred embodiments, the nimodipine formulation is administered as a continuous infusion. In methods of the invention, first pass metabolism by the liver is minimized and bioavailability is improved. Consistent levels of nimodipine are therefore maintained in the plasma and CSF of the (e.g., human) patient. In certain preferred embodiments, the nimodipine infusion concentrate is introduced into an appropriate infusion bag (e.g., 250 ml bag containing saline, dextrose, etc.) and the nimodipine is infused into the human patient over a time period of about 12 hours as a continuous infusion. Bayer's Nimotop® infusion solution is infused via the central vein (probably because the high alcohol content necessitates co-infusion of dextrose and lactate ringer). In contrast, the infusion solution of the present invention is formulated to be infused via the peripheral vein (which is much less invasive than via the central vein). However, the infusion solution of the invention can be infused via the peripheral or central vein.

The present invention relates to a novel pharmaceutical composition containing nimodipine base or any acceptable pharmaceutical salt as active for continuous parenteral administration.

The present invention available in particular in the form of a solution for parenteral administration that is a sterile preservative free premix ready for infusion with no further dilution required prior to administration.

The present invention available in particular in the form of a solution for parenteral administration that is in the form of a concentrated injectable solution which can be diluted down in an appropriate medium (e.g. saline) to a solution for administration by infusion.

As used herein, the term "unit dose" refers to physically discrete units suitable as unitary dosages for mammalian subjects, each unit containing as the active ingredient a predetermined quantity of the nimodipine. Examples of suitable unit doses of nimodipine in accordance with the invention include clear solution or micelles or nano-emulsion in suitable containers, e.g., in a ampule or vial.

The term "comprising" is an inclusive term interpreted to mean containing, embracing, covering or including the elements listed following the term, but not excluding other unrecited elements.

A "therapeutically effective amount" means the amount that, when administered to an animal for treating a disease, is sufficient to effect treatment for that disease.

As used herein, the term "treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

By "stable" it is meant that substantially no degradation of the concentrate intravenous infusion solution (the product) is observed after storage for 1 month at 40° C. In preferred embodiments, the term "stable" with respect to the concentrate intravenous infusion solution comprising the water-insoluble nimodipine and surfactant(s) means that there is less than about 5% degradation (and preferably less than 4%, or less than 3%, or less than 2%, or less than 1.5%, or less than 1% degradation) of the nimodipine and no observable precipitate after storage for 48 hours; or that the nimodipine micelle structure is thermally stable during a terminal sterilization process by autoclaving at 121° C. for 30 minutes, in that the mean diameter of the colloidal structures does not change by more than about 50 nanometer comparing the colloidal structures before and after the terminal sterilization process, or both.

The term "parenteral" as used herein, includes subcutaneous injections, intravenous, intramuscular, intrasternal injection or infusion techniques.

The term "substantially free of organic solvent" and/or "substantially free of alcohol" means that the formulation contains no more than 0.5% organic solution/alcohol, or preferably less than 0.4%, less than 0.3%, less than 0.2%, less than 0.1%, or less than 0.05% organic solvent/alcohol.

The term "substantially free of crystalline nimodipine precipitate" or "substantially without nimodipine precipitate" means that the nimodipine concentrate or diluted nimodipine formulation remains a clear solution and free of all drug precipitation that may be clinically significant (e.g., the formulation would be considered to be safe and effective by a regulatory authority such as the U.S. F.D.A.).

The term "without nimodipine precipitate" means that the nimodipine concentrate or diluted nimodipine formulation remains a clear solution and free of all drug precipitation that may be clinically significant (e.g., the formulation would be considered to be safe and effective by a regulatory authority such as the U.S. F.D.A.).

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

DETAILED DESCRIPTION

Nimodipine is a dihydropyridine calcium antagonist. Nimodipine is isopropyl 2-methoxyethyl 1, 4-dihydro-2, 6-dimethyl-4-(m-nitrophenyl)-3, 5-pyridinedicarboxylate. It has a molecular weight of 418.5 and a molecular formula of $C_{21}H_{26}N_2O_7$. Nimodipine inhibits calcium ion transfer into these cells and thus inhibits contractions of vascular smooth muscle. The contractile processes of smooth muscle cells are dependent upon calcium ions, which enter these cells during depolarization as slow ionic transmembrane currents. In animal experiments, nimodipine had a greater effect on cerebral arteries than on arteries elsewhere in the body perhaps because it is highly lipophilic, allowing it to cross the blood-brain barrier; concentrations of nimodipine as high as 12.5 ng/ml have been detected in the cerebrospinal fluid of nimodipine-treated subarachnoid hemorrhage (SAH) patients. The precise mechanism of action of nimodipine in humans is unknown. Although the clinical studies demonstrate a favorable effect of nimodipine on the severity of neurological deficits caused by cerebral vasospasm following SAH, there is no arteriographic evidence that the drug either prevents or relieves the spasm of these arteries. However, whether or not the arteriographic methodology utilized was adequate to detect a clinically meaningful effect, if any, on vasospasm is unknown.

Nimodipine as a pale yellow crystalline powder almost insoluble in water (2.5 µg/ml, 25° C.) Therefore its intrinsic solubility poses challenges in the development of an injectable pharmaceutical formulation that is concentrated, stable and dilutable. The present invention aims to resolve solubility deficiencies of previously approved nimodipine dosage forms by the development of a robust, stable, and easy to administer nimodipine infusion injection. Another objective of the present invention is to provide the composition and preparation of the nimodipine infusion solution and its administration.

Although the present invention focuses on the drug nimodipine, one skilled in the art will appreciate that the present invention is applicable to other dihydropyridine calcium channel blockers such as amlodipine, aranidipine, azelnidipine, barnidipine, benidipine, cilnidipine, clevidipine, efonidipine, felodipine, isradipine, lacidipine, lercanidipine, manidipine, nicardipine, nifedipine, nilvadipine, nisoldipine, nitrendipine, pranidipine, and the like. For purposes of the present invention, in each instance where the drug nimodipine is mentioned, any of the above drugs or other similar dihydropyridine calcium channel blockers can be substituted in its place, and these drugs are meant to be encompassed by the present disclosure.

Two key aspects of a pharmaceutically acceptable liquid formulation, e.g., for parenteral use, are solubility of the drug in the carrier (solvent) and the stability of the final formulation (including but not limited to the ability of the formulation to prevent the drug from precipitating out of solution). The prior art is replete with examples of excipients used to solubilize poorly water soluble drugs for oral and injectable dosage forms. Such excipients include organic solvents, surfactants, triglycerides, cyclodextrins and phospholipids.

The use of organic solvents such as ethanol is limited for parenteral formulations because of possible precipitation of the active (drug), pain, inflammation and hemolysis upon injection. Ethanol is used for both solubility and stability reasons in the prior commercially available forms of nimodipine. As previously reported herein, the currently marketed nimodipine formulation in Europe includes 23.7% ethanol.

In contrast to prior intravenous nimodipine formulations, the intravenous nimodipine formulation of the present invention is a solution comprising nimodipine, a hydrophilic surfactant and a small quantity of organic solvent, wherein nimodipine is dissolved in a small amount of organic solvent by mixing and further this nimodipine solution is combined with a hydrophilic surfactant to form micelles of nimodipine in a clear solution.

The Concentrate

One aspect of the present invention is directed to a nimodipine injection concentrate. In such embodiments, the nimodipine is mixed with a pharmaceutically acceptable carrier to prepare a concentrated injection solution, suspension, emulsion or complex. Thereafter, an effective amount of a hydrophilic surfactant is added. Optionally, a pharmaceutically acceptable medium for injection is added in a relatively small quantity (e.g., 5 ml) in order to prepare the final nimodipine concentrate formulation.

The nimodipine formulations of the present invention having a low ethanol content may be prepared by dissolving the nimodipine and/or a pharmaceutically acceptable salt thereof in ethanol and (e.g., hydrophilic) surfactant. The concentrate may be prepared by admixing a suitable amount of nimodipine to an organic solvent and the hydrophilic surfactant together for a sufficient period of time to form stable micelles. Thereafter, a suitable pharmaceutical medium for injection (e.g., water for injection) is added to prepare the final nimodipine concentrate formulation. Preferably, the pharmaceutical medium (water) is deoxygenated. The ethanol contained in this solution is then removed at least partially by evaporation under vacuum or by any other suitable means. Examples of other acceptable drying methods include rotavap (rotatory evaporator), and oven dryer at low temperature. Solutions after ethanol evaporation contain from about 0.5 mg/ml to about 50 mg/ml of nimodipine in a mixture containing from about 1% to about 99.5% of hydrophilic surfactant to be prepared as concentrate injection solution which is stable and substantially alcohol free, if not totally alcohol free. The term "substantially alcohol free" is meant for purposes of the present invention that the concentrate contains from about 0 to about 0.5% organic solvent (e.g., alcohol). The term "totally alcohol free" is meant for purposes of the present invention that the concentrate contains from about 0% organic solvent (e.g., alcohol) or levels that are not measureable by typically used techniques, such as gas chromatography. The ethanol is completely, or almost completely, removed via the aforementioned evaporation step. For example, in a preferred embodiment, the concentrate is subjected to lyophilization using a vacuum drying cycle (e.g., a vacuum at about 75-100 millitorr at a suitable temperature (e.g., room temperature of 25° C.) for a suitable time period (e.g., from about 1 to about 20 hours, preferably from about 3 to about 10 hours). After lyophilization, the product is a viscous liquid with little or no alcohol remains. The concentrate and dilution prepared from the concentrate preferably includes a low alcohol content, e.g., preferably less than 300 mg per dose (e.g., per 10 mg dose of nimodipine), and in certain preferred embodiments less than 200 mg alcohol per dose (per 10 mg dose of nimodipine), or less than 100 mg alcohol per dose, or less than 50 mg alcohol per dose, or less than 25 mg alcohol per dose (per 10 mg dose of nimodipine), or less than 10 mg alcohol per dose (per 10 mg dose of nimodipine), or less than 5 mg alcohol per dose (per 10 mg dose of nimodipine). Expressed in another way, in preferred embodiments, the concentrate and dilution prepared from the concentrate preferably includes a low alcohol content, e.g., preferably from about 0 to about 300 mg per dose (e.g., per 10 mg dose of nimodipine), or from about 0 to about 200 mg alcohol per dose (per 10 mg dose of nimodipine), or from about 0 to about 100 mg per dose (e.g., per 10 mg dose of nimodipine), or from about 0 to about 50 mg alcohol per dose (per 10 mg dose of nimodipine), or from about 0 to about 25 mg per dose (e.g., per 10 mg dose of nimodipine), or from about 0 to about 10 mg alcohol per dose (per 10 mg dose of nimodipine), or from about 0 to about 5 mg alcohol per dose (per 10 mg dose of nimodipine). In certain preferred embodiments of the nimodipine injection concentrate, the median particle size of micelles or nano-emulsions ranges from about 0.5 nanometer to about 350 nanometers, or from about 0.5 nm to about 200 nm, or from about 5 nm to about 50 nm. Preferably, the nimodipine concentrate formulation is clear and does not contain a crystal nimodipine precipitate. In certain preferred embodiments, the nimodipine is substantially contained within micelles as a nano-emulsion. The 10 mg dose of nimodipine contained in the concentrate is typically contained in about 5 ml of the concentrate formulation, although the 10 mg dose of nimodipine may be contained in, e.g., from about 0.5 ml to about 10 ml of formulation. After vacuum drying, the nimodipine injection concentrate (containing a 10 mg dose of nimodipine) preferably is about 0.5 ml.

In certain embodiments of the present invention, the hydrophilic surfactant comprises at least about 8% of the formulation in the injection concentrate and at least 0.1% in the final diluted injection solution. In other preferred embodiments, the hydrophilic surfactant comprises from about 1% to about 95.5% of the formulation, by weight of the injection concentrate and from about 0.01% to about 2.5% of the final diluted injection solution.

In certain preferred embodiments, the hydrophilic surfactant comprises a pharmaceutically acceptable non-ionic surfactant. The non-ionic surfactant is preferably included in an amount sufficient to inhibit precipitation of drug substance from the pharmaceutically acceptable medium for injection (e.g., aqueous solution) after dilution. Non-ionic surfactants form stable micelles with drug substance, can solubilize the drug and may impart additional photo stability to the drug.

Using HLB values as a rough guide, hydrophilic surfactants are considered those compounds having an HLB value greater than 10 particularly from 12 to 17. The hydrophilic non-ionic surfactant is more soluble in water than in oil (having HLB higher than 10).

Pharmaceutically acceptable non-ionic surfactants useful in the formulations of the present invention include but are not limited to, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters. Further examples are reaction products of a natural or polyethoxylated castor oil and ethylene oxide. The ethoxylated castor oil may have an ethylene oxide content of 25 to 100 moles ethylene oxide per molecule, preferably 35 to 60 moles ethylene oxide per molecule. The natural or polyethoxylated castor oil may be reacted with ethylene oxide in a molar ratio of from about 1:35 to about 1:60, with optional removal of the polyethoxylated component from the products. Non-ionic hydrophilic surfactants useful in the present invention further include alkylglucosides; alkylmaltosides; alkylthioglucosides; lauryl macrogolglycenides; polyoxyethylene alkyl ethers; polyoxyethylene alkylphenols; polyethylene glycol fatty (mono- and di-) acid esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene sterols and analogues thereof; polyoxyethylene vegetable oils, polyoxyethylene hydrogenated vegetable oils; reaction mixtures of polyols and at least one member selected from the group consisting of fatty acids, glycerides, vegetable oils, hydrogenated vegetable oils, in sterols; sugar esters, sugar ethers; sucroglycerides; fatty acid salts, bile salts, phospholipids, phosphoric acid esters, carboxylates, sulfates, sulfonates. More specifically, the nonionic surfactant may comprise, for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof. Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful.

Examples of the same include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Polyethylene glycol fatty acid esters are also suitable for use as surfactants in the compositions of the present invention, such as PEG-20 dilaurate, PEG-20 dioleate, PEG-20 distearate, PEG-32 dilaurate, PEG-32 dioleate, PEG-20 glyceryl laurate, PEG-30 glyceryl laurate, PEG-40 glyceryl laurate, PEG-20 glyceryl oleate, and PEG-30 glyceryl oleate. The hydrophilic surfactant may further comprise mixtures of any of the foregoing.

Polysorbate 80, an especially preferred hydrophilic non-ionic surfactant in the formulations of the present invention, is a surfactant commonly used in protein parenteral formulations to minimize denaturation at the air-water interface. Polysorbate 80 is also sometimes used in injectable solution formulations of small molecules for the purpose of solubility enhancement due to micelle formation. Polysorbates are nonionic surfactants of sorbitan esters. Polysorbates useful in the present invention include, but are not limited to polysorbate 20, polysorbate 40, polysorbate 60, polysorbate 80 (Tween 80) and any combinations or mixtures thereof. Other suitable preferred surfactants includes poloxamer, poloxamer 407, transcutol. The surfactant can be any surfactant suitable for use in pharmaceutical compositions. Suitable surfactants can also be ionic hydrophilic surfactants or hydrophobic surfactants. Suitable hydrophilic surfactants can be anionic, cationic, zwitterionic or non-ionic, although non-ionic hydrophilic surfactants are presently preferred. Preferably, the nimodipine formulations of the invention include at least one non-ionic hydrophilic surfactant.

However, in other embodiments, the nimodipine formulations may include mixtures of two or more non-ionic hydrophilic surfactants, as well as mixtures containing at least one non-ionic hydrophilic surfactant and at least one hydrophobic surfactant.

In certain embodiments, the surfactant can be one or more of the surfactants described in U.S. Pat. No. 6,363,471, hereby incorporated by reference.

In certain embodiments of the present invention, the organic solvent is an alcohol (e.g., ethanol) and the solubilizer is polysorbate.

In the above embodiments, the nimodipine is solubilized using surface active agents as solubilizers via the formation of colloidal particles called micelles and stabilized by using co-solvents and/or appropriate substrates in the aqueous formulation. This results in the formation of micelles, or minute colloidal particles which surround the nimodipine molecule, isolating it from the water molecules surrounding it, but forming a clear aqueous solution. The liquid formulations are suitable for use as parenteral, nasal or oral administration.

Water-miscible surfactant molecules like polysorbate consists of both hydrophobic and hydrophilic portions that can solubilize select poorly water-soluble drugs. Surfactants can also self-assemble to form micelles once the surfactant monomer concentration reaches the critical micelle concentration. Thus, surfactants can solubilize drug molecules by either a direct co-solvent effect or by uptake into micelles. The non-ionic surfactants in commercially available solubilized oral and injectable formulations include polyoxyl 35 castor oil (Cremophor EL), polyoxyl 40 hydrogenated castor oil (Cremophor RH 40), polysorbate 20 (Tween 20), polysorbate 80 (Tween 80), d-tocopherol polyethylene glycol 1000 succinate (TPGS), Solutol HS-15, sorbitan monooleate (Span 80), polyoxyl 40 stearate, and various polyglycolyzed glycerides including Labrafil M-1944CS, Labrafil M-2125CS, Labrasol, Gellucire 44/14, and Softigen 767.

In the present invention nimodipine formulation preferably forms colloidal structures (micelles) about 10 nm in diameter. In other preferred embodiments, the mean diameter of the colloidal structures varies from about 0.5 nm to about 200 nm and more preferably about 5 nm to about 50 nm. In the present invention, the nimodipine micelle structure is thermally stable during a terminal sterilization process by autoclaving at 121° C. for 30 minutes.

Any suitable pharmaceutically acceptable water-miscible organic solvent can be used in the present invention during the preparation of the nimodipine concentrate formulation, although alcohol is preferred. Selection of a suitable organic solvent will depend in part upon the solubility of the active material (nimodipine) in the solvent, the degree to which the solvent is miscible in water, and the tolerability of the solvent. The solvent should be physiologically acceptable. Examples of solvents that may be used in the present invention include, but are not limited to, various alcohols such as ethanol, glycols, glycerin, propylene glycol, and various polyethylene glycols and dimethyl isosorbide (DMI). Additional useful alcohols include but are not limited to methanol (methyl alcohol), ethanol, (ethyl alcohol), 1-propanol (n-propyl alcohol), 2-propanol (isopropyl alcohol), 1-butanol (n-butyl alcohol), 2-butanol (sec-butyl alcohol), 2-methyl-1-propanol (isobutyl alcohol), 2-methyl-2-propanol (t-butyl alcohol), 1-pentanol (n-pentyl alcohol), 3-methyl-1-butanol (isopentyl alcohol), 2,2-dimethyl-1-propanol (neopentyl alcohol), cyclopentanol (cyclopentyl alcohol), 1-hexanol (n-hexanol), cyclohexanol (cyclohexyl alcohol), 1-heptanol (n-heptyl alcohol), 1-octanol (n-octyl alcohol), 1-nonanol (n-nonyl alcohol), 1-decanol (n-decyl alcohol), 2-propen-1-ol (allyl alcohol), phenylmethanol (benzyl alcohol), diphenylmethanol (diphenylcarbinol), triphenylmethanol (triphenylcarbinol), glycerin, phenol, 2-methoxyethanol, 2-ethoxyethanol, 3-ethoxy-1,2-propanediol, Di(ethylene glycol) methyl ether, 1,2-propanediol, 1,3-propanediol, 1,3-butanediol, 2,3-butanediol, 1,4-butanediol, 1,2-pentanediol, 1,3-pentanediol, 1,4-pentanediol, 1,5-pentanediol, 2,3-pentanediol, 2,4-pentanediol, 2,5-pentanediol, 3,4-, pentanediol, and 3,5-pentanediol.

The nimodipine concentrates of the invention may be contained in any pharmaceutically acceptable container (e.g., ampules, vials) in a unit dose for later dilution (e.g., at the site and time of administration to a human patient).

Dilution

The injectable nimodipine formulations of the invention are preferably clear, colorless and contain the nimodipine in micelles or inclusion complexes, etc. which can be diluted with a pharmaceutically acceptable carrier for injection (e.g., water for injection) to produce a thermodynamically stable dispersion of non-ionic surfactant nanoparticles which are micelles, inclusion complexes, etc., as described and disclosed herein. The diluted nimodipine formulation is stable, i.e., the nimodipine does not phase separate across a broad range of temperatures (e.g., from about 15° C. to about 25° C.) at a wide range of pH (e.g., from about pH 5 to about pH 8). Thus, the nimodipine injection concentrate disclosed herein, when diluted with water for injection, saline, dextrose or commonly available infusion solutions up to a concentration of 0.01 mg/ml remains a clear solution and displays no precipitation of nimodipine. When diluted to 10 times dilution of 0.01 mg/ml, there is preferably still no precipitate (e.g., the limit would be, e.g., about 0.001 mg/ml).

In accordance with the present invention, the nimodipine formulation allows for administration of a single 250 ml infusion bag or bottle that contains IV nimodipine comprising, e.g., less than 2% w/v or less than 1% w/v alcohol in a predominantly aqueous medium, a distinct improvement over IV Nimotop. Preferably, the nimodipine formulation may comprise less than about 0.5% w/v alcohol in 250 ml formulation, as a ready-to-use formulation. This lower alcohol content in the formulation provides many advantages known to those skilled in the art, for example, making the inventive nimodipine formulation amenable for administration to patients suffering from alcoholism, impaired alcohol metabolism and those who are pregnant and breast feeding. Stated another way, the nimodipine concentrate (and therefore the nimodipine diluted solution) of the present invention contains, e.g., from 0 to about 300 mg alcohol.

The present invention is a micellar formulation of nimodipine that provides for greatly enhanced aqueous solubility and stability including photo-stability. Nimodipine does not precipitate out of this formulation even when diluted with water up to 250 times its original concentration. The concentrate has a nimodipine concentration from 10 mg/ml to 50 mg/ml, and that the diluted form has a nimodipine concentration from 0.04 mg/ml to 0.2 mg/ml which can be up to 250 times greater.

In certain embodiments of the present invention, the nimodipine injection concentrate is diluted in an infusion bag containing water for injection or any commonly available intravenous infusion solution. Infusion volumes can range from about 50 ml to about 1000 ml. The current invention provides for dilution of formulation in a single infusion bag and infused over a specific period unlike Bayer's Nimotop intravenous injection which requires a three-way stopcock auxiliary to infuse Nimotop solution along with two other co-infusion solutions to prevent any drug precipitation. The current invention provides for a single infusion solution that does not precipitate upon dilution and/or administration thus improving safety and efficacy.

In certain preferred embodiments, the nimodipine injection can be further diluted to a $2.5 \times 10^{-5}$ mole solution of nimodipine to rinse the exposed arteries after clipping the aneurysm and before an intravenous infusion of nimodipine administered to improve patient outcome.

In certain preferred embodiments, the novel solvent free (e.g., less than 1% w/v organic solvent such as ethanol) nimodipine formulation can be administered intravenous bolus, intravenous infusion, intra-arterial, intraoral, intranasal using a naso-gastric tube.

In certain preferred embodiments, the nimodipine injection after dilution with commonly available infusion solutions, the infusion set and bag can be covered with ultraviolet light (UV) protective bags to further protect it from photo-degradation.

The compounds of the invention may be administered parenterally in formulations eventually containing conventional non-toxic pharmaceutically acceptable carriers, adjuvants and vehicles as desired.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables. Suitable carriers for intravenous administration include physiological saline or phosphate buffered saline (PBS), and solutions containing solubilizing agents, such as glucose, polyethylene glycol, and polypropylene glycol and mixtures thereof.

The aqueous vehicle(s) useful in the nimodipine concentrate and nimodipine solutions of the present invention include, by way of example and without limitation, Sodium Chloride Injection, Ringers Injection, Isotonic Dextrose Injection, Sterile Water Injection, Dextrose, and Lactated Ringers Injection. Nonaqueous parenteral vehicles include, by way of example and without limitation, fixed oils of vegetable origin, cottonseed oil, corn oil, sesame oil and peanut oil.

Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride, benzethonium chloride, boric acid, p-hydroxybenzoates, phenols, chlorinated phenolic compounds, alcohols, quarternary compounds, mercurials, mixtures of the foregoing and the like. Isotonic agents include, by way of example and without limitation, sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80) [A sequestering or chelating agent of metal ions include EDTA.] Pharmaceutically acceptable pH adjusting agents include, by way of example and without limitation, sodium hydroxide, hydrochloric acid, citric acid or lactic acid. The nimodipine formulations of the invention may additionally include physiologically acceptable components such as sodium chloride and like materials conventionally used to achieve isotonicity with typical body fluids, pH buffers to establish a physiologically compatible pH range and to enhance the solubility of the nimodipine, preservatives, stabilizers and antioxidants and the like.

In certain preferred embodiments, the injectable formulations after dilution with water for injection and other commonly available intravenous infusion solutions, the pH of final diluted solution will be from about 3 to about 9, and in certain preferred embodiments from about 4.5 to about 8. In some embodiments of the present invention, the pH is adjusted using a pharmaceutically acceptable buffer or alkalizing agent, with suitable alkalizing agents and buffers including but not limited to NaOH, KOH, triethylamine, meglumine, L-Arginine, sodium phosphate buffer (either sodium phosphate tribasic, sodium phosphate dibasic, sodium phosphate monobasic, or o-phosphoric acid), sodium bicarbonate, and mixtures of any of the foregoing.

In certain other embodiments, the formulation may be made isotonic via the addition of a tonicity agent, such as but not limited to any pharmaceutically acceptable sugar, salt or any combinations or mixtures thereof, such as, but not limited to dextrose and sodium chloride. The tonicity agents may be present in an amount from about 100 mOsm/kg to about 500 mOsm/kg, or from about 200 mOsm/kg to about 400 mOsm/kg, or from about 280 mOsm/kg to about 320 mOsm/kg.

Nimodipine Stability

Drug stability is the ability of the pharmaceutical dosage form to maintain its physical, chemical, therapeutic and microbial properties during the time of storage and usage by the patient. It is measured by the rate of changes that take place in the pharmaceutical dosage forms. Drug dosage can not be used after known and unknown impurity levels exceed the limit, per guidelines set by ICH. In addition, some products of drug degradation are toxic and harmful to patients. Several factors affect drug stability; among them oxidative degradation is one major factor. This oxidative degradation rate is directly proportional to the amount of oxygen available to drug, in the formulation. Temperature increases oxidative degradation. Our experimental studies indicate that a lower concentration of over head space and dissolved oxygen provides additional stability to the nimodipine IV formulation. Deaerated WFI for formulation preparation and inert gas blanketing (purging with an inert gas such as nitrogen) while processing and during the filling process provide a robust stable nimodipine IV drug formulation. To attain a more stable drug formulation, the dissolved oxygen content should be about 2.0 ppm in the nimodipine formulation and headspace oxygen content should be less than 5%. After dilution as described above, the nimodipine formulations of the invention are preferably chemically stable up to at least 48 hours for continuous infusion.

Treatment with Nimodipine

In accordance with the present invention, intravenous nimodipine solution can treat conditions such as, but not limited to, aneurysms, subarachnoid hemorrhage, vasospastic angina, Prinzmetal angina, stable angina, acute myocardial infarction, myocardial arrest, arrhythmia, systemic hypertension, pulmonary hypertension, congestive heart failure, coronary artery surgery and hypertrophic cardiomyopathy.

Nimodipine is indicated for the treatment of ischaemic neurological deficits following aneurysmal subarachnoid haemorrhage. With respect to Nimotop® 0.02% solution for infusion (Bayer plc), the recommended treatment is as follows: for the first two hours of treatment 1 mg of nimodipine, i.e., 5 ml Nimotop solution, (about 15 µg/kg bw/h), should be infused each hour via a central catheter. If it is well tolerated, the dose should be increased after two hours to 2 mg nimodipine, i.e. 10 ml Nimotop solution per hour (about 30 µg/kg bw/h), providing no severe decrease in blood pressure is observed. Patients of body weight less than 70 kg or with unstable blood pressure should be started on a dose of 0.5 mg nimodipine per hour (2.5 ml of Nimotop solution), or less if necessary. Nimotop capsules are also available in the U.S. for oral administration, each one containing 30 mg of nimodipine in a vehicle of glycerin, peppermint oil, purified water and polyethylene glycol 400. The oral dose is 60 mg every 4 hours for 21 consecutive days, preferably not less than one hour before or two hours after meals.

In certain embodiments of the present invention, the IV nimodipine solution can be continuously infused over a period of about 3 weeks. The rate of infusion can be titrated based on patient tolerance and avoiding a decrease in blood pressure. The preferred infusion rate is from about 0.05 mg nimodipine per hour to about 5 mg nimodipine per hour. A dose titration is not possible with currently US FDA approved oral dosage forms.

In certain embodiments of the present invention, the IV nimodipine dose is reduced to about 2 to 10 mg every five hours compared to the current approved oral dose of 60 mg every four hours without reduction in drug product efficacy and safety. The current US FDA approved oral nimodipine drug product has high first-pass metabolism resulting in numerous metabolites, all of which are either inactive or considerably less active than the parent compound. The bioavailability of nimodipine averages 13% after oral administration. The first-pass metabolism is avoided via intravenous administration, and intra-subject (patient) variability associated with current approved oral dosage forms is reduced. Also, the single bag and or bottle continuous intravenous infusion of the nimodipine formulations of the invention is a convenient way to administer the effective concentration of nimodipine to unconscious patient and to patient having difficulty in swallowing oral dosage forms.

DETAILED DESCRIPTION OF PREFERRED EMBODIMENTS

The following examples of formulations in accordance with the present invention are not to be construed as limiting the present invention in any manner and are only samples of the various formulations described herein.

Examples 1-2

The formulation of Example 1-2 was prepared as follows: nimodipine base was added to ethanol while stirring and mixing until a clear solution is observed. Polysorbate 80 was then added as a surfactant while stirring and mixing for 30 minutes to form stable micelles. Sufficient water for injection (deoxygenated water) was then added to the solution to generate 5 ml of nimodipine injection concentrate. The ethanol is then completely, or almost completely, removed by evaporation in a lyophilizer using vacuum drying cycle at room temperature. After lyophilization, the product is a viscous liquid with little or no alcohol remains. In these examples, the lyophilization process includes a vacuum at about 75-100 millitorr at 25° C. until the final product is obtained (little or no alcohol as per the present invention). The ingredients of Examples 1-2 are set forth in Table 1 below:

TABLE 1

| Composition | Example 1 Quantity in mg | Example 2 Quantity in mg |
|---|---|---|
| Concentrate Solution | | |
| Nimodipine | 10 | 10 |
| Alcohol (dehydrated) | 1900 | 1900 |
| Polysorbate 80 | 400 | 400 |
| Water for injection | Qs 5 ml | Qs 5 ml |
| Ethanol Evaporation Process using Lyophilizer | | |
| Process temperature | 25° C. | 25° C. |
| Vacuum applied | 75 millitorr | 100 millitorr |
| Duration of process | 3 hours | 10 hours |

The alcohol content of Examples 1-2 was determined using high pressure liquid chromatography with a refractive index (RI) detector and the results are shown in Table 2. A single dose represents 10 mg of nimodipine infused over 5 hours.

TABLE 2

| | Example 1 (Before ethanol evaporation) | Example 1 (After ethanol evaporation) | Example 2 (After ethanol evaporation) | IV Nimotop ® Infusion |
|---|---|---|---|---|
| Ethanol concentration per dose | 1867 mg/dose | 263 mg/dose | 1.88 mg/dose | 10416 mg/dose |

Examples 3

The concentrated formulation of Example 2 with ethanol content about 2 mg/dose was reconstituted with sterile 0.9% sodium chloride solution up to 100 ml volume and filled in the amber color glass bottle. The composition of the formulation is further detailed in Table 3 below:

TABLE 3

| Composition | Qty/dose |
|---|---|
| Concentrated formulation of example 2 | Equivalent to 10 mg of Nimodipine |
| 0.9% Sodium chloride | Quantity sufficient up to 100 mL |
| Total | 100 mL |

Example 4

Amber glass bottles were filled with the formulation of Example 2 (Concentrate) and Example 3 (100 mL ready to infuse) with a rubber stopper and flip-off seal and subjected to stability under following conditions:
  ICH accelerated conditions (ACC) at 40° C.±2° C./75% RH±5% RH; and
  ICH room temperature conditions (CRT) at 25° C.±2° C./60% RH±5% RH
The International Council for Harmonisation of Technical Requirements for Pharmaceuticals for Human Use (ICH) is a project that brings together the regulatory authorities of Europe, Japan and the United States and experts from the pharmaceutical industry.

Samples were analyzed to measure the Nimodipine assay, impurities and physical stability (drug precipitation during stability). The stability data is provided in Table 4 below.

TABLE 4

| Test | Specification | Example 2 (Concentrate) | | | | Example 3 (Ready to use) | | |
|---|---|---|---|---|---|---|---|---|
| | | Initial | 1M ACC | 3M ACC | 6M CRT | Initial | 3M ACC | 6M ACC |
| Physical Appearance | Free of drug precipitation | Y | Y | Y | Y | Y | Y | Y |
| Assay by HPLC | 90.0-110.0% | 95.0% | 99.2% | 100.1% | 97.7% | 99.4% | 95.1% | 101.4% |
| Total Impurities | NMT 2.0% | <1.0% | <1.0% | <1.0% | <1.0% | <1.0% | <1.0% | <1.0% |
| Ethanol Content | NMT 50 mg/dose | <2.0 mg/dose | | | | <2.0 mg/dose | | |

Y—Complies

CONCLUSION

It will be apparent to those skilled in the art that the nimodipine concentrate and diluted formulations may be made using different but equivalent methods, and that these formulations may use other surfactants, carriers and emulsifiers beyond those specifically mentioned herein. Such obvious modifications are considered to be within the scope of the appended claims.

What is claimed is:

1. A method of treatment, comprising administering a therapeutically effective dose of a nimodipine concentrate formulation to a human patient suffering from a condition selected from the group consisting of aneurysms, subarachnoid hemorrhage, vasospastic angina, Prinzmetal angina, stable angina, acute myocardial infarction, myocardial arrest, arrhythmia, systemic hypertension, pulmonary hypertension, congestive heart failure, coronary artery surgery and hypertrophic cardiomyopathy, wherein the nimodipine concentrate formulation consists of:
(a) an aqueous carrier,
(b) nimodipine base or a pharmaceutically acceptable salt of nimodipine at a concentration from about 10 mg/ml to about 50 mg/ml in the aqueous carrier,
(c) an effective amount of a hydrophilic surfactant consisting of polysorbate 80,
(d) from about 0 to about 0.5% organic solvent,
(e) an optional preservative, and
(f) an optional buffering agent,
and wherein the nimodipine concentrate formulation is clear, colorless, stable, and without crystalline nimodipine precipitate.

2. The method of claim 1, wherein the nimodipine in the nimodipine concentrate formulation is contained in micelles, and the micelles have a median particle size that ranges from about 0.5 nm to about 350 nm.

3. The method of claim 1, wherein from about 0.5 ml to about 10 ml of the nimodipine concentrate formulation is administered to the human patient.

4. The method of claim 1, wherein the polysorbate 80 comprises from about 40% to about 99% of the nimodipine concentrate formulation.

5. The method of claim 1, wherein the nimodipine concentrate formulation contains from about 0 to about 300 mg of the organic solvent.

6. The method of claim 1, wherein the nimodipine concentrate formulation contains from about 0 to about 100 mg of the organic solvent per dose per 10 mg dose of nimodipine, and the organic solvent is alcohol.

7. The method of claim 1, wherein the organic solvent is dehydrated alcohol, and the aqueous carrier is water for injection.

8. The method of claim 7, wherein the nimodipine concentrate formulation contains from about 0 to about 100 mg of the dehydrated alcohol per dose per 10 mg dose of nimodipine.

9. The method of claim 1, wherein the nimodipine concentrate formulation (i) is stable for at least 3 months when stored under ICH accelerated conditions (ACC) at 40° C.±2° C./75% RH±5% RH, or (ii) is stable for at least 6 months when stored under ICH room temperature conditions (CRT) at 25° C.±2° C./60% RH±5% RH, or (iii) is stable for at least 3 months when stored under ICH accelerated conditions (ACC) at 40° C.±2° C./75% RH±5% RH and is stable for at least 6 months when stored under ICH room temperature conditions (CRT) at 25° C.±2° C./60% RH±5% RH.

10. The method of claim 1, wherein, prior to the administration, the nimodipine concentrate formulation is diluted in an aqueous carrier to a concentration from about 0.001 mg/ml to about 0.5 mg/ml.

11. The method of claim 1, wherein the nimodipine concentrate formulation consists of the nimodipine base or the pharmaceutically acceptable salt of nimodipine, the hydrophilic surfactant consisting of polysorbate 80, the aqueous carrier and the organic solvent, wherein the organic solvent is an alcohol.

* * * * *